US011345691B2

(12) United States Patent
Schils et al.

(10) Patent No.: US 11,345,691 B2
(45) Date of Patent: May 31, 2022

(54) PRODRUG MODULATORS OF THE CYSTIC FIBROSIS TRANSMEMBRANE CONDUCTANCE REGULATOR PROTEIN AND METHODS OF USE

(71) Applicants: AbbVie Global Enterprises Ltd., Hamilton (BM); Galapagos NV, Mechelen (BE)

(72) Inventors: Didier Philippe Robert Schils, Mechelen (BE); Sam Bob Corveleyn, Mechelen (BE); Herman Augustinus De Kock, Mechelen (BE); Matthew Beau Dufek, Hartland, WI (US)

(73) Assignees: AbbVie Global Enterprises Ltd., Hamilton (BM); Galapagos NV, Mechelen (BE)

( * ) Notice: Subject to any disclaimer, the term of this patent is extended or adjusted under 35 U.S.C. 154(b) by 23 days.

(21) Appl. No.: 16/890,035

(22) Filed: Jun. 2, 2020

(65) Prior Publication Data
US 2020/0377491 A1 Dec. 3, 2020

Related U.S. Application Data

(60) Provisional application No. 62/856,273, filed on Jun. 3, 2019.

(51) Int. Cl.
C07D 413/04 (2006.01)
A61K 45/06 (2006.01)

(52) U.S. Cl.
CPC ............ C07D 413/04 (2013.01); A61K 45/06 (2013.01)

(58) Field of Classification Search
CPC .................................................. C07D 413/04
See application file for complete search history.

(56) References Cited

U.S. PATENT DOCUMENTS 8,999,976 B2 4/2015 Binch et al.
9,981,910 B2 5/2018 Altenbach et al.
10,399,940 B2 9/2019 Altenbach et al.

FOREIGN PATENT DOCUMENTS

| WO | WO-2005120497 A2 | 12/2005 |
|----|------------------|---------|
| WO | WO-2006002421 A2 | 1/2006 |
| WO | WO-2008147952 A1 | 12/2008 |
| WO | WO-2009074575 A2 | 6/2009 |
| WO | WO-2009076593 A1 | 6/2009 |
| WO | WO-2010048573 A1 | 4/2010 |
| WO | WO-2011072241 A1 | 6/2011 |
| WO | WO-2011113894 A1 | 9/2011 |
| WO | WO-2012048181 A1 | 4/2012 |
| WO | WO-2013038373 A1 | 3/2013 |
| WO | WO-2013038378 A1 | 3/2013 |
| WO | WO-2013038381 A1 | 3/2013 |
| WO | WO-2013038386 A1 | 3/2013 |
| WO | WO-2013038390 A1 | 3/2013 |
| WO | WO-2013043720 A1 | 3/2013 |
| WO | WO-2014180562 A1 | 11/2014 |
| WO | WO-2015018823 A1 | 2/2015 |
| WO | WO-2015138909 A1 | 9/2015 |
| WO | WO-2015138934 A1 | 9/2015 |
| WO | WO-2016069757 A1 | 5/2016 |
| WO | WO-2016069891 A1 | 5/2016 |
| WO | WO-2016193812 A1 | 12/2016 |
| WO | WO-2017009804 A1 | 1/2017 |
| WO | WO-2017060873 A1 | 4/2017 |
| WO | WO-2017060874 A1 | 4/2017 |
| WO | WO-2017187321 A1 | 11/2017 |
| WO | WO-2017208115 A1 | 12/2017 |
| WO | WO-2018116185 A1 | 6/2018 |

OTHER PUBLICATIONS

FDA Drug Safety Communication, 2017, pp. 1-2.*
Bobadilla J.L., et al., "Cystic Fibrosis: a Worldwide Analysis of Cftr Mutations—Correlation With Incidence Data and Application To Screening," Human mutation, 2002, vol. 19 (6), pp. 575-606.
Cross L.C., et al., "IUPAC Commission on Nomenclature of Organic Chemistry: Rules for the Nomenclature of Organic Chemistry Section E: Stereochemistry (Recommendations 1974)," Pure and Applied Chemistry, 1976, Pergamon Press, Great Britain, vol. 45, pp. 11-30.
Furniss B.S., et al., Vogel's Textbook of Practical Organic Chemistry, 5th Edition, Longman Scientific & Technical, 1989, Essex CM20 2JE, England, Table of Contents.

* cited by examiner

Primary Examiner — Samira J Jean-Louis
(74) Attorney, Agent, or Firm — Quarles & Brady LLP

(57) ABSTRACT

The present invention relates to prodrug compounds and their use in the treatment of Cystic Fibrosis, methods for their production, pharmaceutical compositions comprising the same, and methods of treating cystic fibrosis by administering a compound of the invention.

3 Claims, No Drawings

PRODRUG MODULATORS OF THE CYSTIC FIBROSIS TRANSMEMBRANE CONDUCTANCE REGULATOR PROTEIN AND METHODS OF USE

TECHNICAL FIELD

This invention relates to prodrug compounds that are modulators of the Cystic Fibrosis Transmembrane Conductance Regulator (CFTR) protein, useful in treating diseases and conditions mediated and modulated by CFTR. This invention also relates to compositions containing compounds of the invention, processes for their preparation, and methods of treatment using them.

BACKGROUND OF THE INVENTION

Cystic fibrosis is the most common fatal genetic disease in humans, and affects ~0.04% of white individuals (Bobadilla, J. L., Macek, M., Jr, Fine, J. P., Farrell, P. M., 2002. Cystic fibrosis: a worldwide analysis of CFTR mutations—correlation with incidence data and application to screening. Hum. Mutat. 19, 575-606. doi:10.1002/humu.10041), for example, in the United States, about one in every 2,500 infants is affected, and up to 10 million people carry a single copy of the defective gene without apparent ill effects. In contrast, individuals with two copies of the CF associated gene suffer from the debilitating and fatal effects of CF, including chronic lung infections.

Accordingly, there is a need for deliverable novel compounds able to modulate CFTR.

BRIEF SUMMARY OF THE INVENTION (5-{3-Amino-5-[4-(trifluoromethoxy)benzene-1-sulfonyl]pyridin-2-yl}-1,3,4-oxadiazol-2-yl)methanol is currently in clinical development for the treatment of Cystic Fibrosis and can reach targeted plasma levels but was unexpectedly found to have low blood exposure, which may require a high pill burden. Surprisingly, it has been identified that certain prodrugs of (5-{3-amino-5-[4-(trifluoromethoxy)benzene-1-sulfonyl]pyridin-2-yl}-1,3,4-oxadiazol-2-yl)methanol achieve significantly greater exposure. The present invention discloses prodrug compounds that act as CFTR modulators. The present invention also provides methods for the preparation of these compounds, pharmaceutical compositions comprising these compounds and methods for the treatment of cystic fibrosis by administering the compounds of the invention.

The invention provides for prodrug compounds of 5-{3-amino-5-[4-(trifluoromethoxy)benzene-1-sulfonyl]pyridin-2-yl}-1,3,4-oxadiazol-2-yl)methanol with better exposure.

In one embodiment, the prodrug compound is (5-{3-amino-5-[4-(trifluoromethoxy)benzene-1-sulfonyl]pyridin-2-yl}-1,3,4-oxadiazol-2-yl)methyl (dimethylamino)acetate, or a pharmaceutically acceptable salt thereof.

In one embodiment, the prodrug compound is (5-{3-amino-5-[4-(trifluoromethoxy)benzene-1-sulfonyl]pyridin-2-yl}-1,3,4-oxadiazol-2-yl)methyl 3-(dimethylamino)propanoate, or a pharmaceutically acceptable salt thereof.

In one embodiment, the prodrug compound is (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof.

Another aspect of the invention relates to pharmaceutical compositions comprising the prodrug compounds of the invention, and a pharmaceutical carrier. Such compositions can be administered in accordance with a method of the invention, typically as part of a therapeutic regimen for treatment or prevention of Cystic Fibrosis.

These and other objects of the invention are described in the following paragraphs. These objects should not be deemed to narrow the scope of the invention.

DETAILED DESCRIPTION OF THE INVENTION

Described herein are prodrug compounds of 5-{3-amino-5-[4-(trifluoromethoxy)benzene-1-sulfonyl]pyridin-2-yl}-1,3,4-oxadiazol-2-yl)methanol. Further, compositions comprising such compounds and methods for treating conditions and disorders using such compounds and compositions are also included.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds.

Compounds

Compounds disclosed herein are prodrugs of (5-{3-amino-5-[4-(trifluoromethoxy)benzene-1-sulfonyl]pyridin-2-yl}-1,3,4-oxadiazol-2-yl)methanol, a potent modulator of the Cystic Fibrosis Transmembrane Conductance Regulator (CFTR) protein.

One embodiment pertains to prodrug compounds of (5-{3-amino-5-[4-(trifluoromethoxy)benzene-1-sulfonyl]pyridin-2-yl}-1,3,4-oxadiazol-2-yl)methanol, or a pharmaceutically acceptable salt thereof.

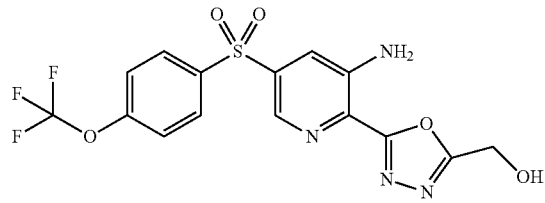 [SMILES: Nc1cc(S(=O)(=O)c2ccc(OC(F)(F)F)cc2)cnc1-c1nnc(CO)o1]

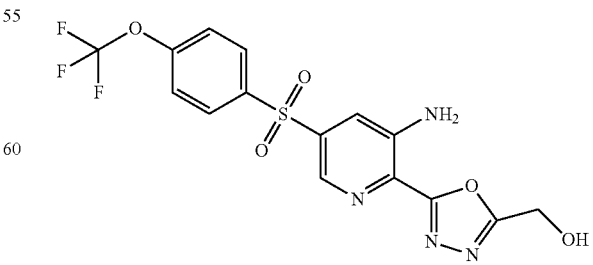

Another embodiment pertains to (5-{3-amino-5-[4-(trifluoromethoxy)benzene-1-sulfonyl]pyridin-2-yl}-1,3,4-oxadiazol-2-yl)methyl (dimethylamino)acetate

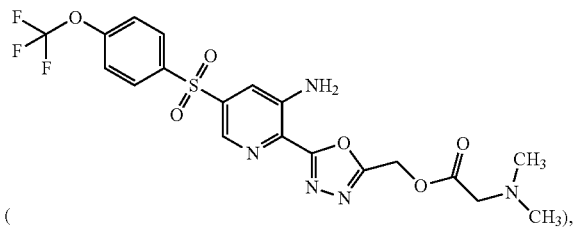

or a pharmaceutically acceptable salt thereof.

Another embodiment pertains to (5-{3-amino-5-[4-(trifluoromethoxy)benzene-1-sulfonyl]pyridin-2-yl}-1,3,4-oxadiazol-2-yl)methyl 3-(dimethylamino)propanoate ( )

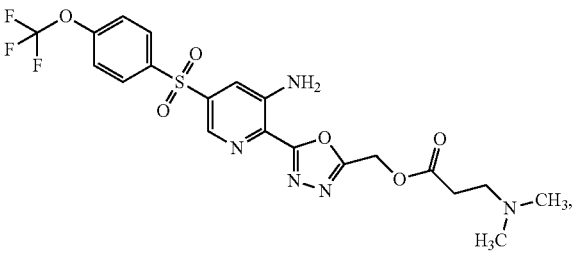 [SMILES: CN(C)CCC(=O)OCc1nnc(-c2ncc(S(=O)(=O)c3ccc(OC(F)(F)F)cc3)cc2N)o1]

or a pharmaceutically acceptable salt thereof.

Another embodiment pertains to (5-{3-amino-5-[4-(trifluoromethoxy)benzene-1-sulfonyl]pyridin-2-yl}-1,3,4-oxadiazol-2-yl)methyl (2S)-2-amino-3-methylbutanoate

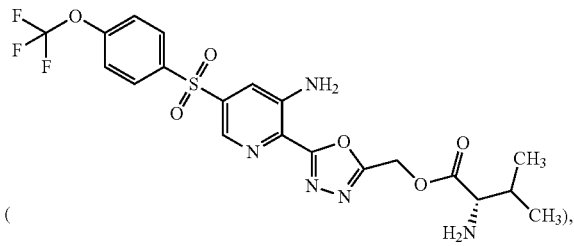

or a pharmaceutically acceptable salt thereof.

Compounds of the invention were named using Name 2017.2.1 (File Version N40E41, Build 96719, 6 Sep. 2017) naming algorithm by Advanced Chemical Development, Inc., or Struct=Name naming algorithm as part of CHEMDRAW® Professional Version 15.0.0.106.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may be attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of the invention wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labelled compounds of the invention for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of the invention may generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of the invention may contain either a basic or an acidic functionality, or both, and can be converted to a pharmaceutically acceptable salt, when desired, by using a suitable acid or base. The salts may be prepared in situ during the final isolation and purification of the compounds of the invention.

The invention contemplates compounds of the invention formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

When employed as a pharmaceutical, a compound of the invention is typically administered in the form of a pharmaceutical composition. The phrase "pharmaceutical composition" refers to a composition suitable for administration in medical use.

The term "pharmaceutically acceptable carrier" as used herein, means a non-toxic, inert solid, semi-solid or liquid filler, diluent, encapsulating material or formulation auxiliary of any type.

Methods of Use

The compounds and compositions may be administered to a subject for the treatment or prevention of cystic fibrosis.

Compounds of the invention are useful as modulators of CFTR. Thus, the compounds and compositions are particularly useful for treating or lessening the severity or progression of a disease, disorder, or a condition where hyperactivity or inactivity of CFTR is involved. Accordingly, the invention provides a method for treating cystic fibrosis with or without a pharmaceutically acceptable carrier. In one embodiment, the cystic fibrosis is caused by a Class I, II, III, IV, V, and/or VI mutation.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303L) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G, G1349D, S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326delTC, or 4279insA mutations. More particularly, Class VI mutation(s) refers to Rescued F508del mutations.

The present invention provides compounds of the invention, or a pharmaceutically acceptable salt thereof, or a pharmaceutical composition comprising a compound of the invention, for use in medicine. In one embodiment, the present invention provides compounds of the invention or pharmaceutical compositions comprising a compound of the invention, for use in the treatment of cystic fibrosis. In one embodiment, the present invention provides 5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, for use in the treatment of cystic fibrosis. In a more particular embodiment, the cystic fibrosis is caused by a Class I, II, III, IV, V, and/or VI mutation.

This invention also is directed to the use of 5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, in the manufacture of a medicament for the treatment of cystic fibrosis. In a more particular embodiment, the cystic fibrosis is caused by a Class I, II, III, IV, V, and/or VI mutation.

In one embodiment, the present invention provides pharmaceutical compositions comprising a compound of the invention, or a pharmaceutically acceptable salt thereof, and one or more additional therapeutic agents. In another embodiment, the present invention provides pharmaceutical compositions comprising a compound of the invention, or a pharmaceutically acceptable salt thereof, and one or more additional therapeutic agents wherein the additional therapeutic agents are selected from CFTR modulators and CFTR amplifiers. In another embodiment, the present invention provides pharmaceutical compositions comprising a compound of the invention, or a pharmaceutically acceptable salt thereof, and one or more additional therapeutic agents wherein the additional therapeutic agents are CFTR modulators. In one embodiment, the present invention provides pharmaceutical compositions comprising 5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, and one or more additional therapeutic agents where in the additional therapeutic agents are CFTR modulators.

In one embodiment, the present invention provides pharmaceutical compositions comprising a compound of the invention, or a pharmaceutically acceptable salt thereof, one potentiator, and one or more additional correctors. In one embodiment, the present invention provides pharmaceutical compositions comprising 5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, one potentiator, and one or more additional correctors.

In one embodiment, the present invention provides a method for treating cystic fibrosis in a subject comprising administering a compound of the invention, or a pharmaceutically acceptable salt thereof, and one or more additional therapeutic agents. In another embodiment, the present invention provides a method for treating cystic fibrosis in a subject comprising administering a compound of the invention, or a pharmaceutically acceptable salt thereof, and one or more additional therapeutic agents selected from CFTR modulators and CFTR amplifiers. In one embodiment, the present invention provides a method for treating cystic fibrosis in a subject comprising administering a compound of the invention, or a pharmaceutically acceptable salt thereof, and one or more additional therapeutic agents wherein the additional therapeutic agents are CFTR modulators. In another embodiment, the other therapeutic agent is a cystic fibrosis treatment agent. In a particular embodiment, the additional therapeutic agent(s) are one potentiator, and one or more additional correctors. In another embodiment, the additional therapeutic agent(s) is selected from CFTR modulators and CFTR amplifiers. In another embodiment, the other therapeutic agent(s) is a CFTR modulator. In a more particular embodiment, the cystic fibrosis is caused by a Class I, II, III, IV, V, and/or VI mutation. In one embodiment, the present invention provides a method for treating cystic fibrosis in a subject comprising administering 5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, and one or more additional therapeutic agents.

The present compounds or pharmaceutically acceptable salts thereof may be administered as the sole active agent or it may be co-administered with other therapeutic agents, including other compounds or pharmaceutically acceptable salts thereof, that demonstrate the same or a similar therapeutic activity and that are determined to be safe and efficacious for such combined administration. The present compounds may be co-administered to a subject. Two or more different therapeutic agents can be co-administered to a subject in a single pharmaceutical composition or in separate pharmaceutical compositions. Two or more different therapeutic agents can be co-administered at the same time as a single pharmaceutical composition comprising these therapeutic agents or at different times.

The compounds of the invention or pharmaceutically acceptable salts thereof may be co-administered with one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers In one embodiment, the CFTR mediated disease is cystic fibrosis.

In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulators. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of CFTR potentiators include, but are not limited to, Ivacaftor (VX-770), CTP-656, NVS-QBW251, FD1860293, GLPG2451, GLPG3067, GLPG1837, PTI-808, N-(3-carbamoyl-5,5,7,7-tetramethyl-5,7-dihydro-4H-thieno[2,3-c]pyran-2-yl)-1H-pyrazole-5-carboxamide, and 3-amino-N-[(2S)-2-hydroxypropyl]-5-{[4-(trifluoromethoxy)phenyl]sulfonyl}pyridine-2-carboxamide.

Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823, WO2014/180562, WO2015018823, WO 2016193812 and WO2017208115.

In one embodiment, the potentiator can be selected from the group consisting of

Ivacaftor (VX-770, N-(2,4-di-tert-butyl-5-hydroxyphenyl)-4-oxo-1,4-dihydroquinoline-3-carboxamide);
GLPG1837;
GLP-2451;
PTI-808;
CTP-656;
NVS-QBW251,
FD1860293
GLPG3067;
2-(2-fluorobenzamido)-5,5,7,7-tetramethyl-5,7-dihydro-4H-thieno[2,3-c]pyran-3-carboxamide;

N-(3-carbamoyl-5,5,7,7-tetramethyl-4,7-dihydro-5H-thieno
[2,3-c]pyran-2-yl)-1H-pyrazole-5-carboxamide;
2-(2-hydroxybenzamido)-5,5,7,7-tetramethyl-5,7-dihydro-
4H-thieno[2,3-c]pyran-3-carboxamide
2-(1-hydroxycyclopropanecarboxamido)-5,5,7,7-tetram-
ethyl-5,7-dihydro-4H-thieno[2,3-c]pyran-3-carboxamide;
5,5,7,7-tetramethyl-2-(2-(trifluoromethyl)benzamido)-5,7-
dihydro-4H-thieno[2,3-c]pyran-3-carboxamide;
2-(2-hydroxy-2-methylpropanamido)-5,5,7,7-tetramethyl-5,
7-dihydro-4H-thieno[2,3-c]pyran-3-carboxamide;
2-(1-(hydroxymethyl)cyclopropanecarboxamido)-5,5,7,7-
tetramethyl-5,7-dihydro-4H-thieno[2,3-c]pyran-3-car-
boxamide;
2-(3-hydroxy-2,2-dimethylpropanamido)-5,5,7,7-tetram-
ethyl-5,7-dihydro-4H-thieno[2,3-c]pyran-3-carboxamide;
N-(3-carbamoyl-5,5,7,7-tetramethyl-5,7-dihydro-4H-thieno
[2,3-c]pyran-2-yl)-5-methyl-1H-pyrazole-3-carboxam-
ide;
N-(3-carbamoyl-5,5,7,7-tetramethyl-5,7-dihydro-4H-thieno
[2,3-c]pyran-2-yl)-5-cyclopropyl-1H-pyrazole-3-carbox-
amide;
N-(3-carbamoyl-5,5,7,7-tetramethyl-5,7-dihydro-4H-thieno
[2,3-c]pyran-2-yl)-5-isopropyl-1H-pyrazole-3-carboxam-
ide;
N-(3-carbamoyl-5,5,7,7-tetramethyl-5,7-dihydro-4H-thieno
[2,3-c]pyran-2-yl)-5-(trifluoromethyl)-1H-pyrazole-3-
carboxamide;
5-tert-butyl-N-(3-carbamoyl-5,5,7,7-tetramethyl-5,7-di-
hydro-4H-thieno[2,3-c]pyran-2-yl)-1H-pyrazole-3-car-
boxamide;
N-(3-carbamoyl-5,5,7,7-tetramethyl-5,7-dihydro-4H-thieno
[2,3-c]pyran-2-yl)-5-ethyl-1H-pyrazole-3-carboxamide;
N-(3-carbamoyl-5,5,7,7-tetramethyl-5,7-dihydro-4H-thieno
[2,3-c]pyran-2-yl)-3-ethyl-4-methyl-1H-pyrazole-5-car-
boxamide;
2-(2-hydroxypropanamido)-5,5,7,7-tetramethyl-5,7-di-
hydro-4H-thieno[2,3-c]pyran-3-carboxamide;
N-(3-carbamoyl-5,5,7,7-tetramethyl-5,7-dihydro-4H-thieno
[2,3-c]pyran-2-yl)-4-chloro-1H-pyrazole-3-carboxamide;
N-(3-carbamoyl-5,5,7,7-tetramethyl-5,7-dihydro-4H-thieno
[2,3-c]pyran-2-yl)-1,4,6,7-tetrahydropyrano[4,3-c]pyra-
zole-3-carboxamide;
4-bromo-N-(3-carbamoyl-5,5,7,7-tetramethyl-5,7-dihydro-
4H-thieno[2,3-c]pyran-2-yl)-1H-pyrazole-3-carboxam-
ide;
N-(3-carbamoyl-5,5,7,7-tetramethyl-5,7-dihydro-4H-thieno
[2,3-c]pyran-2-yl)-4-chloro-5-methyl-1H-pyrazole-3-car-
boxamide;
N-(3-carbamoyl-5,5,7,7-tetramethyl-5,7-dihydro-4H-thieno
[2,3-c]pyran-2-yl)-4-methyl-1H-pyrazole-3-carboxam-
ide;
2-(2-hydroxy-3,3-dimethylbutanamido)-5,5,7,7-tetram-
ethyl-5,7-dihydro-4H-thieno[2,3-c]pyran-3-carboxamide;
2-[(2-hydroxy-4-methyl-pentanoyl)amino]-5,5,7,7-tetram-
ethyl-4H-thieno[2,3-c]pyran-3-carboxamide;
5-(2-methoxy-ethoxy)-1H-pyrazole-3-carboxylic acid
(3-carbamoyl-5,5,7,7-tetram ethyl-4,7-dihydro-5H-thieno
[2,3-c]pyran-2-yl)-amide;
N-(3-carbamoyl-5,5,7,7-tetramethyl-4H-thieno[2,3-c]
pyran-2-yl)-4-(3-methoxypropyl)-1H-pyrazole-3-carbox-
amide;
N-(3-carbamoyl-5,5,7,7-tetramethyl-4H-thieno[2,3-c]
pyran-2-yl)-4-(2-ethoxyethyl)-1H-pyrazole-3-carboxam-
ide;
2-[[(2S)-2-hydroxy-3,3-dimethyl-butanoyl]amino]-5,5,7,7-
tetramethyl-4H-thieno[2,3-c]pyran-3-carboxamide;
2-[[(2R)-2-hydroxy-3,3-dimethyl-butanoyl]amino]-5,5,7,7-
tetramethyl-4H-thieno[2,3-c]pyran-3-carboxamide;
2-[(2-hydroxy-2,3,3-trimethyl-butanoyl)amino]-5,5,7,7-te-
tramethyl-4H-thieno[2,3-c]pyran-3-carboxamide;
[5-[(3-carbamoyl-5,5,7,7-tetramethyl-4H-thieno[2,3-c]
pyran-2-yl)carbamoyl]pyrazol-1-yl]methyl dihydrogen
phosphate;
[3-[(3-carbamoyl-5,5,7,7-tetramethyl-4H-thieno[2,3-c]
pyran-2-yl)carbamoyl]pyrazol-1-yl]methyl dihydrogen
phosphate;
N-(3-carbamoyl-5,5,7,7-tetramethyl-4H-thieno[2,3-c]
pyran-2-yl)-4-(1,4-dioxan-2-yl)-1H-pyrazole-3-carbox-
amide;
5,5,7,7-tetramethyl-2-[[(2S)-3,3,3-trifluoro-2-hydroxy-2-
methyl-propanoyl]amino]-4H-thieno[2,3-c]pyran-3-car-
boxamide;
2-[[(2S)-2-hydroxypropanoyl]amino]-5,5,7,7-tetramethyl-
4H-thieno[2,3-c]pyran-3-carboxamide;
3-amino-N-(2-hydroxy-2-methylpropyl)-5-{[4-(trifluo-
romethoxy)phenyl]sulfonyl}pyridine-2-carboxamide;
3-amino-N-[(4-hydroxy-1-methylpiperidin-4-yl)methyl]-5-
{[4-(trifluoromethoxy)phenyl]sulfonyl}pyridine-2-car-
boxamide;
3-amino-N-(3-hydroxy-2,2-dimethylpropyl)-5-{[4-(trifluo-
romethoxy)phenyl]sulfonyl}pyridine-2-carboxamide;
3-amino-5-[(4-fluorophenyl)sulfonyl]-N-[(1-hydroxycyclo-
propyl)methyl]pyridine-2-carboxamide;
3-amino-5-[(4-fluorophenyl)sulfonyl]-N-[(2R)-3,3,3-trif-
luoro-2-hydroxypropyl]pyridine-2-carboxamide;
3-amino-5-[(3-fluorophenyl)sulfonyl]-N-(2-hydroxy-2-
methylpropyl)pyridine-2-carboxamide;
3-amino-N-[4-(cyclopropylamino)-2-oxoethyl]-5-{[4-(trif-
luoromethoxy)phenyl]sulfonyl}pyridine-2-carboxamide;
(3-amino-5-{[4-(trifluoromethoxy)phenyl]
sulfonyl}pyridin-2-yl)(azetidin-1-yl)methanone;
(3-amino-5-{[4-(trifluoromethoxy)phenyl]
sulfonyl}pyridin-2-yl) [3-(hydroxymethyl)azetidin-1-yl]
methanone;
(3-amino-5-{[4-(trifluoromethoxy)phenyl]
sulfonyl}pyridin-2-yl)(3-fluoroazetidin-1-yl)methanone;
3-amino-N-[(2R)-2-hydroxy-3-methoxypropyl]-5-{[4-(trif-
luoromethyl)phenyl]sulfonyl}pyridine-2-carboxamide;
(3-amino-5-{[2-fluoro-4-(trifluoromethoxy)phenyl]
sulfonyl}pyridin-2-yl)(3-hydroxyazetidin-1-yl)metha-
none;
(3-amino-5-{[2-(trifluoromethoxy)phenyl]
sulfonyl}pyridin-2-yl)(3,3-difluoroazetidin-1-yl)metha-
none;
rac-3-amino-N-[(3R,4S)-4-hydroxytetrahydro-2H-pyran-3-
yl]-5-{[2-(trifluoromethoxy)phenyl]sulfonyl}pyridine-2-
carboxamide;
3-amino-5-[(4,4-difluoropiperidin-1-yl)sulfonyl]-N-(3,3,3-
trifluoro-2-hydroxypropyl)pyridine-2-carboxamide;
(3-amino-5-{[2-(trifluoromethoxy)phenyl]
sulfonyl}pyridin-2-yl)[3-hydroxy-3-(trifluoromethyl)
azetidin-1-yl]methanone;
3-amino-N-(2-hydroxy-4-methylpentyl)-5-{[4-(trifluo-
romethoxy)phenyl]sulfonyl}pyridine-2-carboxamide;
(3-amino-5-{[4-(trifluoromethyl)phenyl]sulfonyl}pyridin-
2-yl)(3-hydroxy-3-methylazetidin-1-yl)methanone;
3-amino-N-(3,3,3-trifluoro-2-hydroxypropyl)-5-{[4-(trif-
luoromethyl)piperidin-1-yl]sulfonyl}pyridine-2-carbox-
amide;
3-amino-N-[2-hydroxy-1-(4-methoxyphenyl)ethyl]-5-{[4-
(trifluoromethoxy)phenyl]sulfonyl}pyridine-2-carbox-
amide;

3-amino-5-[(3,3-difluoroazetidin-1-yl)sulfonyl]-N-(3,3,3-trifluoro-2-hydroxypropyl)pyridine-2-carboxamide;
3-amino-5-{[2-fluoro-4-(trifluoromethyl)phenyl]sulfonyl}-N-[(2S)-2-hydroxypropyl]pyridine-2-carboxamide;
3-amino-5-{[2-fluoro-4-(trifluoromethyl)phenyl]sulfonyl}-N-[(2R)-2-hydroxy-3-methoxypropyl]pyridine-2-carboxamide;
3-amino-N-[2-oxo-2-(propan-2-ylamino)ethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3R)-tetrahydrofuran-3-ylmethyl]pyridine-2-carboxamide;
(3-amino-5-{[2-fluoro-4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3S)-tetrahydrofuran-3-ylmethyl]pyridine-2-carboxamide;
3-amino-5-{[2-fluoro-4-(trifluoromethoxy)phenyl]sulfonyl}-N-[(3S)-tetrahydrofuran-3-ylmethyl]pyridine-2-carboxamide;
3-amino-N-[2-hydroxy-3-(2,2,2-trifluoroethoxy)propyl]-5-{[4-(trifluoromethyl)phenyl]sulfonyl}pyridine-2-carboxamide;
3-amino-N-(3-tert-butoxy-2-hydroxypropyl)-5-{[2-fluoro-4-(trifluoromethyl)phenyl]sulfonyl}pyridine-2-carboxamide;
[3-amino-5-(phenylsulfonyl)pyridin-2-yl][3-hydroxy-3-(trifluoromethyl)azetidin-1-yl]methanone;
{3-amino-5-[(3-fluorophenyl)sulfonyl]pyridin-2-yl}[3-hydroxy-3-(trifluoromethyl)azetidin-1-yl]methanone; and
3-amino-N-[(2S)-2-hydroxypropyl]-5-{[4-(trifluoromethoxy)phenyl]sulfonyl}pyridine-2-carboxamide.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2851, GLPG2222, GLPG2665, GLPG2737, GLPG3221, PTI-801, VX-152, VX-440, VX-445, VX-659, FDL169, FDL304, FD2052160, and FD2035659. Examples of correctors are also disclosed in WO2016069757, WO02016069891, WO2017009804, WO2017060874, WO2017060873, WO2017187321 and U.S. patent application Ser. No. 15/723,896, Ser. No. 15/726,075 and PCT Patent Application No. PCT/IB2017/058179.

In one embodiment, the corrector(s) can be selected from the group consisting of
Lumacaftor (VX-809);
1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);
PTI-801;
VX-983;
GLPG2665;
GLPG2851;
GLPG2222;
GLPG2737;
GLPG3221;
VX-152;
VX-440;
VX-659;
VX-445;
FDL169
FDL304;
FD2052160;
FD2035659;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;
3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;
3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;
3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;
3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;
3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;
3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;
4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;
4-[(2R,4R)-4-({[1-(2,2-difluoro-1,3-benzodioxol-5-yl)cyclopropyl]carbonyl}amino)-3,4-dihydro-2H-chromen-2-yl]benzoic acid;
4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;
rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl) cyclopropyl]carbonyl}amino)tetrahydro-2H-pyran-2-yl] benzoic acid;

3-[(2S,4R)-4-({[1-(2,2-difluoro-1,3-benzodioxol-5-yl)cyclopropyl]carbonyl}amino)tetrahydro-2H-pyran-2-yl] benzoic acid;

3-[(2R,4S)-4-({[1-(2,2-difluoro-1,3-benzodioxol-5-yl)cyclopropyl]carbonyl}amino)tetrahydro-2H-pyran-2-yl] benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl) cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl) cyclopropyl]carbonyl}amino)-6-phenyltetrahydro-2H-pyran-2-yl]benzoic acid;

4-[(2R,4S)-4-({[1-(2,2-difluoro-1,3-benzodioxol-5-yl)cyclopropyl]carbonyl}amino)tetrahydro-2H-pyran-2-yl] benzoic acid;

3-cyclobutyl-4-[4-(morpholin-4-yl)piperidin-1-yl]-1-phenyl-1H-pyrazolo[3,4-b]pyridine-6-carboxylic acid;

3-cyclobutyl-1-phenyl-4-{4-[(pyrrolidin-1-yl)methyl]piperidin-1-yl}-1H-pyrazolo[3,4-b]pyridine-6-carboxylic acid;

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid;

6-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl] pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl] amino}-7-(trifluoromethoxy)-3,4-dihydro-2H-1-benzopyran-2-yl]cyclohexane-1-carboxylic acid;

6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl] pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl] amino}-7-methoxy-3,4-dihydro-2H-1-benzopyran-2-yl] cyclohexane-1-carboxylic acid;

ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;

cis-4-[(2R,4R)-4-{[(7R)-2,2-difluoro-7-methyl-6,7-dihydro-2H-furo[2,3-f][1,3]benzodioxole-7-carbonyl] amino}-7-(trifluoromethoxy)-3,4-dihydro-2H-1-benzopyran-2-yl]cyclohexane-1-carboxylic acid;

trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;

1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl] cyclopropane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl] amino}-7-(trifluoromethoxy)-3,4-dihydro-2H-1-benzopyran-2-yl]cyclohexane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl] amino}-7-methoxy-3,4-dihydro-2H-1-benzopyran-2-yl] cyclohexane-1-carboxylic acid;

trans-4-[(2R,4R)-4-{[(7R)-2,2-difluoro-7-methyl-6,7-dihydro-2H-furo[2,3-f][1,3]benzodioxole-7-carbonyl] amino}-7-methoxy-3,4-dihydro-2H-1-benzopyran-2-yl] cyclohexane-1-carboxylic acid;

trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid; and trans-4-[(2R,4R)-4-{[(7R)-2,2-difluoro-7-methyl-6,7-dihydro-2H-furo[2,3-f][1,3]benzodioxole-7-carbonyl] amino}-7-(trifluoromethoxy)-3,4-dihydro-2H-1-benzopyran-2-yl]cyclohexane-1-carboxylic acid.

In one embodiment, the present invention features a method of cystic fibrosis comprising co-administering (5-{3-amino-5-[4-(trifluoromethoxy)benzene-1-sulfonyl] pyridin-2-yl}-1,3,4-oxadiazol-2-yl)methyl (2S)-2-amino-3-methylbutanoate, or a pharmaceutically acceptable salt thereof, with one or two CFTR modulators and one CFTR amplifier. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof with one potentiator, one or more correctors, and one CFTR amplifier. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with one or more CFTR modulators. In one embodiment, the present invention features a method of treating cystic fibrosis comprising co-administering (5-{3-amino-5-[4-(trifluoromethoxy)benzene-1-sulfonyl] pyridin-2-yl}-1,3,4-oxadiazol-2-yl)methyl (2S)-2-amino-3-methylbutanoate, or a pharmaceutically acceptable salt thereof, with one CFTR modulators. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with two CFTR modulators. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with three CFTR modulators. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with one potentiator and one or more correctors. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with one potentiator and two correctors. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with one potentiator. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with one or more correctors. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with one corrector. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with two correctors. In one embodiment, the corrector is 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid, or a pharmaceutically acceptable salt thereof.

In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with one or more correctors, wherein one of the correctors is 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid, or a pharmaceutically acceptable salt thereof. In one embodiment, the present invention features a method of treating cystic fibrosis comprising co-administering (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, with 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid, or a pharmaceutically acceptable salt thereof.

In one embodiment, a combination comprises (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof, and 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid, or a pharmaceutically acceptable salt thereof.

In one embodiment, the present invention features a combination comprising (5-{3-amino-5-[4-(trifluoromethoxy)benzene-1-sulfonyl]pyridin-2-yl}-1,3,4-oxadiazol-2-yl)methyl (2S)-2-amino-3-methylbutanoate and an additional therapeutic agent, wherein the additional therapeutic agent is a CFTR amplifier. CFTR amplifiers enhance the effect of known CFTR modulators, such as potentiators and correctors. Examples of CFTR amplifiers are PTI130 and PTI-428. Examples of amplifiers are also disclosed in International Patent Publication Nos.: WO2015138909 and WO2015138934.

In one embodiment, the additional therapeutic agent is a CFTR stabilizer. CFTR stabilizers enhance the stability of corrected CFTR that has been treated with a corrector, corrector/potentiator or other CFTR modulator combination(s). An example of a CFTR stabilizer is cavosonstat (N91115). Examples of stabilizers are also disclosed in International Patent Publication No.: WO2012048181.

In one embodiment, the present invention features a combination comprising (5-{3-amino-5-[4-(trifluoromethoxy)benzene-1-sulfonyl]pyridin-2-yl}-1,3,4-oxadiazol-2-yl)methyl (2S)-2-amino-3-methylbutanoate and an additional therapeutic agent, wherein the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in International Patent Publication Nos. WO2009074575 and WO2013043720; and U.S. Pat. No. 8,999,976.

In one embodiment, the present invention features a combination comprising (5-{3-amino-5-[4-(trifluoromethoxy)benzene-1-sulfonyl]pyridin-2-yl}-1,3,4-oxadiazol-2-yl)methyl (2S)-2-amino-3-methylbutanoate and an ENaC inhibitor, wherein the ENaC inhibitor is VX-371.

In one embodiment, the present invention features a combination comprising (5-{3-amino-5-[4-(trifluoromethoxy)benzene-1-sulfonyl]pyridin-2-yl}-1,3,4-oxadiazol-2-yl)methyl (2S)-2-amino-3-methylbutanoate and an ENaC inhibitor, wherein the ENaC inhibitor is SPX-101 (S18).

This invention also is directed to kits that comprise one or more compounds and/or salts of the invention, and, optionally, one or more additional therapeutic agents.

This invention also is directed to methods of use of the compounds, salts, compositions, and/or kits of the invention to, with or without one or more additional therapeutic agents, for example, modulate the Cystic Fibrosis Transmembrane Conductance Regulator (CFTR) protein, and treat a disease treatable by modulating the Cystic Fibrosis Transmembrane Conductance Regulator (CFTR) protein.

Chemical Synthetic Procedures

General

The compounds of the invention can be prepared from readily available starting materials using the following general methods and procedures. Additionally, as will be apparent to those skilled in the art, conventional protecting groups may be necessary to prevent certain functional groups from undergoing undesired reactions.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). $^1$H NMR spectra were recorded on a Bruker Advance 300 NMR spectrometer (300 MHz), an Agilent 400 MHz NMR spectrometer or a 500 MHz spectrometer. Chemical shifts (δ) for $^1$H NMR spectra were reported in parts per million (ppm) relative to tetramethylsilane (δ 0.00) or the appropriate residual solvent peak, i.e. CHCl$_3$ (δ 7.27), as internal reference. Multiplicities were given as singlet (s), doublet (d), doublet of doublets of doublets (ddd), doublet of doublets of doublets of doublets (dddd), doublet of doublets of quartets (ddq), doublet of doublets of triplets (ddt), doublet of quartets (dq), doublet of triplets of doublets (dtd), heptet (hept), triplet (t), triplet of doublets of doublets (tdd), triplet of quartets (tq), quartet (q), quartet of doublets (qd), quartet of triplets (qt), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 μm, 2.1 mm ID×50 mm L; Waters Acquity UPLC BEH C18 1.7 μm, 2.1 mm ID×30 mm L; or Waters Xterra® MS 5 μm C18, 100×4.6 mm. The methods were using either MeCN/H$_2$O gradients (H$_2$O contains either 0.1% TFA or 0.1% NH$_3$) or CH$_3$OH/H$_2$O gradients (H$_2$O contains 0.05% TFA). Microwave heating was performed with a Biotage® Initiator.

Racemic mixtures were separated on an Agilent HP1100 system with UV detection. Column used: Chiralpak® IA (10×250 mm, 5 μm). Solvents used: iPrOH and tBME. Enantiomeric purity was determined on an Agilent HP1100 system with UV detection. Column used: Chiralpak® IA (4.6×250 mm, 5 μm). Solvents used: iPrOH and tBME.

List of Abbreviations Used in the Experimental Section

| Abbreviation | Definition |
| --- | --- |
| MeCN | acetonitrile |
| TFA | trifluoroacetic acid |

-continued

| Abbreviation | Definition |
| --- | --- |
| NMR | nuclear magnetic resonance |
| DMSO | dimethyl sulfoxide |
| LC/MS or LCMS | liquid chromatography-mass spectrometry |
| MeOH | methanol |
| tBME | tert-butyl methyl ether |
| s | singlet |
| br s | broad singlet |
| d | duplet or doublet |
| dd | double duplet or doublet of doublets |
| m | multiplet |
| min | minute |
| mL | milliliter |
| μL | microliter |
| g | gram |
| mg | milligram |
| mmol | millimoles |
| HPLC | high pressure liquid chromatography or high performance liquid chromatography |
| ppm | parts per million |
| μm | Micrometer |
| eq. | equivalents |
| w/v | weight/volume |
| w/w | weight/weight |

Synthetic Preparation of the Compounds of the Invention

Schemes

The compounds of the present disclosure can be better understood in connection with the following synthetic schemes and methods which illustrate a means by which the compounds can be prepared. The compounds of this disclosure can be prepared by a variety of synthetic procedures.

Scheme 1

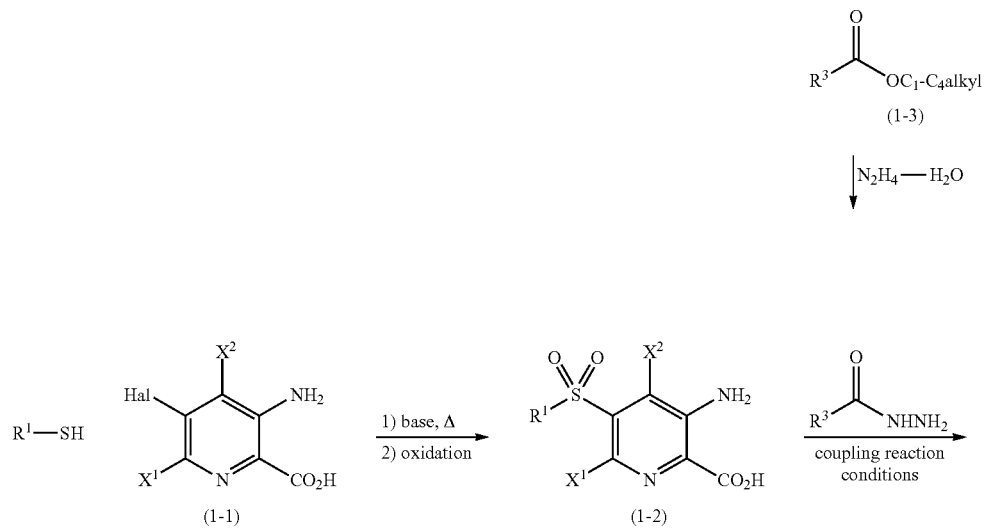

Scheme 1 shows that compounds of formula (1-6) can be prepared from compounds of formula (1-1) wherein $X^1$ and $X^2$ are independently selected

H;

halo;

$C_{1-4}$ alkyl optionally substituted with one or more independently selected halo;

$C_{1-4}$ alkoxy optionally substituted with one or more independently selected

—OH;

$C_{1-4}$ alkoxy; or

—NR$^{8A}$R$^{8B}$;

—NR$^{9A}$R$^{9B}$;

cylopropyl optionally substituted with one or more independently selected R$^5$ groups;

phenoxy optionally substituted with one or more independently selected R$^5$ groups; or phenyl optionally substituted with one or more independently selected R$^5$ groups;

$R^1$ is $C_{1-4}$ alkyl optionally substituted with one or more independently selected

—OH;

$C_{1-4}$ alkoxy; or 4-6 membered monocyclic heterocycle comprising 1 or 2 heteroatoms independently selected from the group consisting of O, S, and N;

phenyl optionally substituted with one or more independently selected R$^4$ groups;

N-linked 4-6 membered monocyclic heterocycle comprising 1, 2, or 3 heteroatoms independently selected from the group consisting of N, O, and S, wherein the monocyclic heterocycle is optionally substituted with one or more independently selected R$^5$ groups;

N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with one or more independently selected R$^5$ groups;

$C_{3-7}$ cycloalkyl optionally substituted with one or more independently selected R$^5$ groups;

—NR$^6$R$^7$;

$R^2$ is 5-6 membered monocyclic heteroaryl comprising 1, 2, or 3 heteroatoms independently selected from the group consisting of O, S, and N, wherein the monocyclic heteroaryl is optionally substituted with one or more independently selected R$^3$ groups;

each R$^3$ is independently selected from the group consisting of:

$C_{1-4}$ alkyl optionally substituted with one or more independently selected $C_{3-7}$ cycloalkyl; wherein the $C_{3-7}$ cycloalkyl is optionally substituted with one or more independently selected R$^4$ groups;

4-6 membered monocyclic heterocycle comprising 1 or 2 heteroatoms independently selected from the group consisting of O, S, and N; wherein the monocyclic heterocycle is optionally substituted with one or more independently selected R$^4$ groups;

phenyl; wherein the phenyl is optionally substituted with one or more independently selected R$^4$ groups;

$C_{1-4}$ alkoxy optionally substituted with one or more independently selected $C_{3-7}$ cycloalkyl, halo, or —OCH$_3$;

—OR$^{11}$;

—OH;

halo;

—CN;

—OC(O)R$^{10}$;

—OS(O)$_2$OH;

—NHC(=S)R$^{11}$; or

—OP(O)(OH)(OH);

—C(O)NH$_2$;

phenyl; wherein the phenyl is optionally substituted with one or more independently selected R$^4$ groups;

5-6 membered monocyclic heteroaryl comprising 1, 2, or 3 heteroatoms independently selected from the group consisting of O, S, and N; wherein the monocyclic heteroaryl is optionally substituted with one or more independently selected R$^4$ groups;

$C_{3-7}$ cycloalkyl; wherein the $C_{3-7}$ cycloalkyl is optionally substituted with one or more independently selected R$^4$ groups; and 4-6 membered monocyclic heterocycle comprising 1 or 2 heteroatoms independently selected from the group consisting of O, S, and N; wherein the monocyclic heterocycle is optionally substituted with one or more independently selected R$^4$ groups;

each R$^4$ is independently selected from the group consisting of:

halo;

$C_{1-4}$ alkyl optionally substituted with one or more independently selected halo; and $C_{1-4}$ alkoxy optionally substituted with one or more independently selected halo;

each R$^5$ is independently selected from the group consisting of:

—OH;

halo;

$C_{1-4}$ alkyl optionally substituted with one or more independently selected $C_{1-4}$ alkoxy, halo or —OH; and $C_{1-4}$ alkoxy optionally substituted with one or more independently selected halo;

$R^6$ is H, $C_{1-4}$ alkyl, or $C_{3-7}$ cycloalkyl wherein the $C_{3-7}$ cycloalkyl is optionally substituted with one or more independently selected $R^5$ groups;

$R^7$ is
$C_{1-4}$ alkyl optionally substituted with one or more independently selected halo;
phenyl optionally substituted with one or more independently selected
halo;
$C_{1-4}$ alkyl optionally substituted with one or more independently selected halo; or
$C_{1-4}$ alkoxy optionally substituted with one or more independently selected halo;
$C_{1-4}$ alkoxy optionally substituted with one or more independently selected halo; or
4-6 membered monocyclic heterocycle comprising 1 or 2 heteroatoms independently selected from the group consisting of O, S, and N; wherein the monocyclic heterocycle is optionally substituted with one or more independently selected $R^5$ groups;
each $R^{8a}$ and $R^{8b}$ is independently selected from the group consisting of
H; and
$C_{1-4}$ alkyl;
$R^{9a}$ and $R^{9b}$ are independently selected from the group consisting of
H;
$C_{1-4}$ alkyl; and
$C_{3-7}$ cycloalkyl;
each $R^{10}$ is independently selected from the group consisting of
$C_{1-6}$ alkyl; and
phenyl; wherein phenyl is optionally substituted with one or more independently selected $R^4$ groups;
each $R^{11}$ is independently selected from the group consisting of
4-6 membered monocyclic heterocycle comprising 1 or 2 heteroatoms independently selected from the group consisting of O, S, and N; wherein the monocyclic heterocycle is optionally substituted with one or more independently selected $R^4$ groups;
5-6 membered monocyclic heteroaryl comprising 1, 2, or 3 heteroatoms independently selected from the group consisting of O, S, and N; wherein the monocyclic heteroaryl is optionally substituted with one or more independently selected $R^4$ groups;
$C_{3-7}$ cycloalkyl; wherein the $C_{3-7}$ cycloalkyl is optionally substituted with one or more independently selected $R^4$ groups; and
phenyl; wherein phenyl is optionally substituted with one or more independently selected $R^4$ groups; and
each $R^4$ is independently selected from the group consisting of
—CN,
halo;
$C_{1-4}$ alkyl optionally substituted with one or more independently selected halo; and
$C_{1-4}$ alkoxy optionally substituted with one or more independently selected halo.

Compounds of formula (1-1), wherein Hal is a halogen, can be reacted first with thiols ($R^1$—SH) in the presence of a base such as 1,8-diazabicyclo[5.4.0]undec-7-ene or potassium carbonate in a solvent such as but not limited to N,N-dimethylacetamide, heated either conventionally or with microwave irradiation to give intermediate thioethers. The intermediate thioethers can be oxidized in a second step with hydrogen peroxide in a solvent such as cooled trifluoroacetic acid to give compounds of formula (1-2). Carboxylic acids of formula (1-2) can be coupled with acylhydrazines of formula (1-4) to give compounds of formula (1-5). Examples of conditions known to generate compounds of formula (1-5) from a mixture of a carboxylic acid and an acylhydrazine include, but are not limited to, adding a coupling reagent such as, but not limited to, N-(3-dimethylaminopropyl)-N'-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b] pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to 4-(dimethylamino) pyridine (DMAP), 1-hydroxy-7-azabenzotriazole (HOAT) and 1-hydroxybenzotriazole (HOBT). The reaction may be carried out optionally in the presence of a base such as, but not limited to, triethylamine, N,N-diisopropylethylamine or pyridine. The coupling reaction may be carried out in solvents such as, but not limited to, tetrahydrofuran, N,N-dimethylformamide, N,N-dimethylacetamide, dimethyl sulfoxide, dichloromethane, and ethyl acetate. The reactions may be carried out at ambient temperature or heated. The heating can be accomplished either conventionally or with microwave irradiation. Acylhydrazines of formula (1-4) are either commercially available or prepared from esters of formula (1-3). Esters of formula (1-3) can be treated with hydrazine hydrate in a solvent such as but not limited to heated tetrahydrofuran. Compounds of formula (1-5) can be dehydrated by treatment with p-toluenesulfonyl chloride and a base such as triethylamine in a solvent such as but not limited to dichloromethane to give compounds of formula (1-6). The $R^3$ substituent may be further manipulated under reaction conditions known to one of skill in the art to give additional $R^3$ substituents. (5-{3-Amino-5-[4-(trifluoromethoxy)benzene-1-sulfonyl]pyridin-2-yl}-1,3,4-oxadiazol-2-yl)methanol (1) is representative of compounds of formula (1-6).

Scheme 2

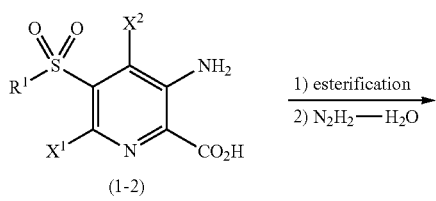

(1-2)

23

-continued

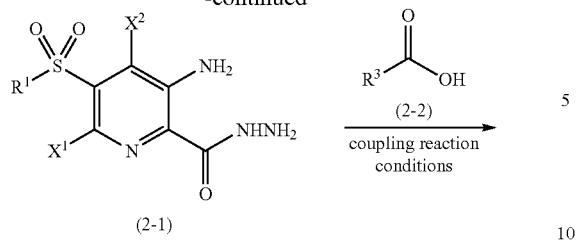

(2-1)

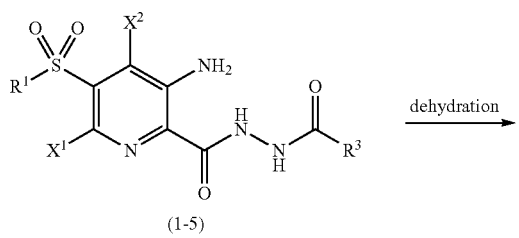

(1-5)

24

-continued

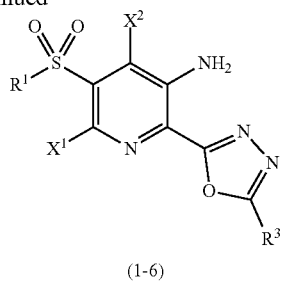

(1-6)

As shown in Scheme 2, compounds of formula (1-6) can be prepared from compounds of formula (1-2) in an alternative to the sequence shown in Scheme 1, wherein $R^1$, $R^3$, $X^1$ and $X^2$ are as defined above. Compounds of formula (1-2) can be converted to compounds of formula (2-1) in a two-step process. In the first step, compounds of formula (1-2) can be esterified by combining compounds of formula (1-2) with methanol or ethanol in the presence of an acid catalyst such as but not limited to sulfuric acid. Heating the mixture provides intermediate esters. Said intermediate esters can be treated in a second step with hydrazine hydrate in a heated solvent such as tetrahydrofuran to give compounds of formula (2-1). Compounds of formula (2-1) can be coupled to compounds of formula (2-2) using the conditions described in Scheme 1 to couple a carboxylic acid to an acylhydrazine to give compounds of formula (1-5). Compounds of formula (1-5) can be dehydrated as described in Scheme 1 to give compounds of formula (1-6). 5-{3-Amino-5-[4-(trifluoromethoxy)benzene-1-sulfonyl]pyridin-2-yl}-1,3,4-oxadiazol-2-yl)methanol (1) is representative of compounds of formula (1-6).

Scheme 3

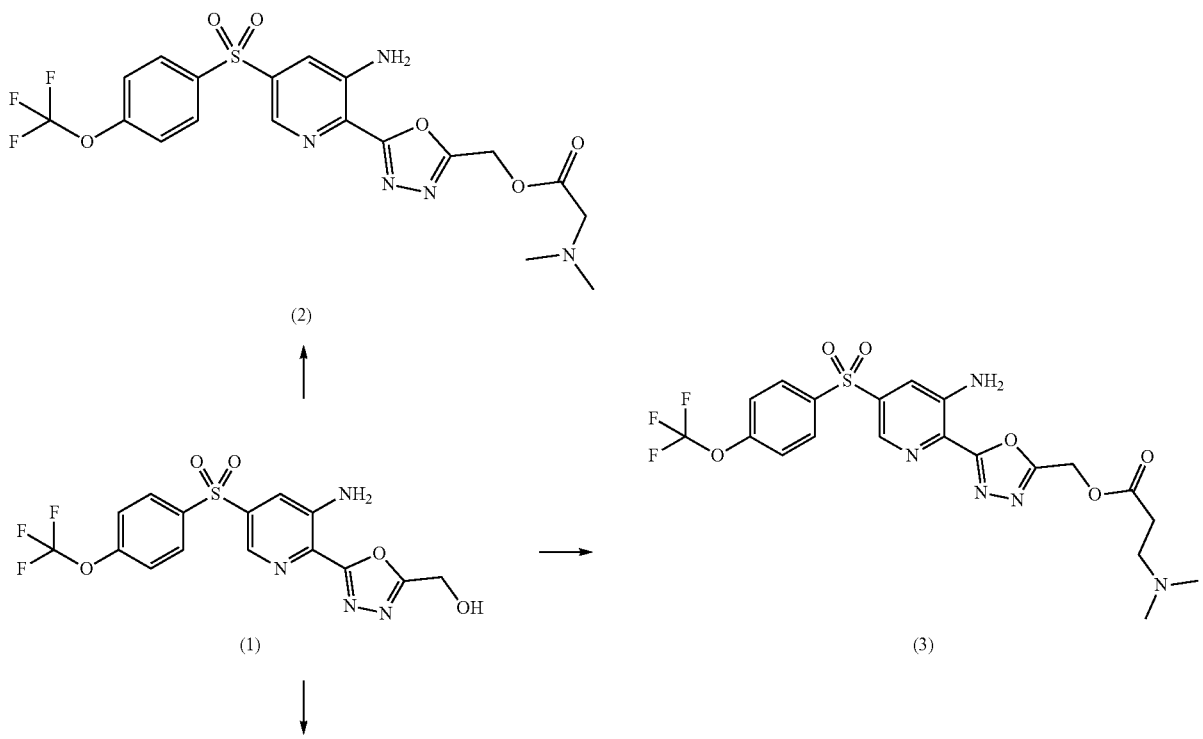

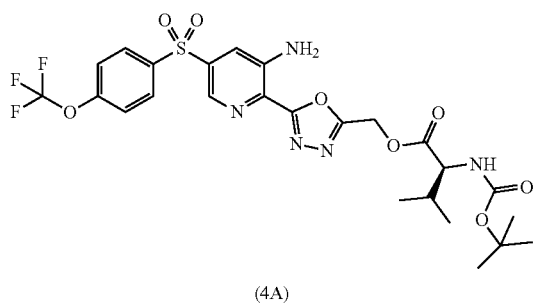

(4A)

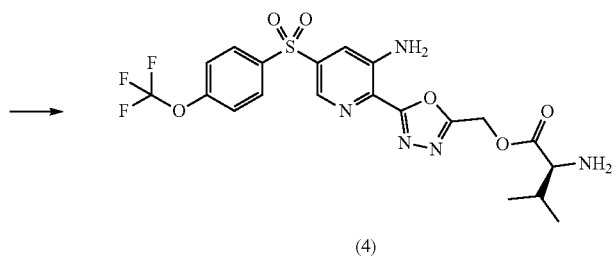

(4)

Prodrug derivatives (Examples (2), (3) and (4)) of (5-{3-amino-5-[4-(trifluoromethoxy)benzene-1-sulfonyl]pyridin-2-yl}-1,3,4-oxadiazol-2-yl)methanol (1) can be prepared as described in Scheme 3. (5-{3-Amino-5-[4-(trifluoromethoxy)benzene-1-sulfonyl]pyridin-2-yl}-1,3,4-oxadiazol-2-yl)methanol (1), prepared as described in Schemes 1 and 2, can be coupled with N,N-dimethylglycine hydrochloride at ambient temperature to provide (5-{3-amino-5-[4-(trifluoromethoxy)benzene-1-sulfonyl]pyridin-2-yl}-1,3,4-oxadiazol-2-yl)methyl (dimethylamino)acetate (2). The reaction typically employs the use of coupling reagents such as but not limited to 1-ethyl-3-[3-(dimethylamino)propyl]-carbodiimide hydrochloride and 4-(dimethylamino) pyridine, and a solvent such as but not limited to dichloromethane. (5-{3-Amino-5-[4-(trifluoromethoxy)benzene-1-sulfonyl]pyridin-2-yl}-1,3,4-oxadiazol-2-yl)methyl 3-(dimethylamino)propanoate (3) can be prepared in a similar manner by coupling (5-{3-amino-5-[4-(trifluoromethoxy)benzene-1-sulfonyl]pyridin-2-yl}-1,3,4-oxadiazol-2-yl)methanol (1) with N,N-dimethyl-β-alanine hydrochloride. (5-{3-Amino-5-[4-(trifluoromethoxy)benzene-1-sulfonyl]pyridin-2-yl}-1,3,4-oxadiazol-2-yl)methyl (2S)-2-amino-3-methylbutanoate (4) can be prepared in a similar manner by coupling (5-{3-amino-5-[4-(trifluoromethoxy)benzene-1-sulfonyl]pyridin-2-yl}-1,3,4-oxadiazol-2-yl)methanol (1) with N-(tert-butoxy carbonyl)-L-valine, followed by deprotection with an acid such as but not limited to trifluoroacetic acid.

EXAMPLES

Example 1

(5-{3-amino-5-[4-(trifluoromethoxy)benzene-1-sulfonyl]pyridin-2-yl}-1,3,4-oxadiazol-2-yl)methanol Step 1: 3-Amino-5-(4-trifluoromethoxy-phenylsulfanyl)-pyridine-2-carboxylic Acid A solution of 3-amino-5-bromo-pyridine-2-carboxylic acid (CAS: 870997-85-6, 3.26 g, 15 mmol), 4-(trifluoromethoxy)benzene-1-thiol (CAS: 169685-29-4, 3.5 g, 18 mmol) and 1,8-diazabicyclo[5.4.0]undec-7-ene (DBU, 2.22 mL, 15 mmol) was prepared in N,N-dimethylacetamide (15 mL). The mixture was heated at 140° C. for 45 minutes in a microwave reactor. The mixture was diluted with a mixture of 1% acetic acid in water. A suspension was obtained that was subsequently filtered. The collected solid was washed with a 1% acetic acid/water mixture and washed with petroleum ether. After drying in a vacuum oven, the title compound was obtained. $^1$H NMR (400 MHz, DMSO-$d_6$) δ ppm 7.68 (d, J=2.0 Hz, 1H), 7.64-7.60 (m, 2H), 7.48-7.44 (m, 2H), 6.99 (d, J=2.0 Hz, 1H).

Step 2: 3-Amino-5-(4-trifluoromethoxy-benzenesulfonyl)-pyridine-2-carboxylic acid 3-Amino-5-(4-trifluoromethoxy-phenylsulfanyl)-pyridine-2-carboxylic acid (12.5 g, 40 mmol, Step 1) was dissolved in trifluoroacetic acid (80 mL), and the resulting mixture was cooled to 0° C. with an ice bath. Next, $H_2O_2$ (14 mL, 160 mmol) was added, and the mixture was stirred at 0° C. until the reaction was finished. The mixture was diluted with a mixture of 1% acetic acid in water. A suspension was obtained that was subsequently filtered. The collected solid was washed with a 1% acetic acid/water mixture and then washed with petroleum ether. After drying in a vacuum oven, the title compound was obtained. MS (ESI+) m/z 363 [M+H]$^+$; $^1$H NMR NMR (400 MHz, DMSO-$d_6$) δ ppm 8.26 (d, J=1.9 Hz, 1H), 8.14 (d, J=8.8 Hz, 2H), 7.79 (d, J=1.9 Hz, 1H), 7.65 (d, J=8.4 Hz, 2H).

Step 3: 3-amino-N'-(hydroxyacetyl)-5-[4-(trifluoromethoxy)benzene-1-sulfonyl]pyridine-2-carbohydrazide To a 40 mL vial was added 3-amino-5-(4-trifluoromethoxy-benzenesulfonyl)-pyridine-2-carboxylic acid (0.50 g, 1.311 mmol, Step 2) and N,N-dimethylformamide (3 mL). 1-[Bis(dimethylamino)methylene]-1H-1,2,3-triazolo[4,5-b]pyridinium 3-oxid hexafluorophosphate (HATU, 0.548 g, 1.442 mmol) was then added, and the resulting solution was stirred for 30 minutes at room temperature. The solution was then transferred via cannula into another 20 mL vial which contained 2-hydroxyacetohydrazide (0.154 g, 1.704 mmol) in N,N-dimethylformamide (3 mL). N,N-Dimethylformamide (1 mL) was added as a rinse. Hunig's base (0.458 mL, 2.62 mmol) was then added dropwise, and the mixture was stirred for 30 minutes at room temperature. Ethyl acetate (20 mL) and 5% aqueous $NaHCO_3$ (20 mL) were added, the resulting biphasic mixture was stirred for 5 minutes, and the layers were separated. The aqueous layer was extracted with ethyl acetate (20 mL). The combined organic extracts were washed with water (2×20 mL) and brine (20 mL), dried over $Na_2SO_4$, filtered, and then concentrated in vacuo to give the title compound, which was used without additional purification (470 mg). $^1$H NMR (501 MHz, DMSO-$d_6$) δ ppm 3.93 (d, J=5.9 Hz, 2H), 5.48 (t, J=6.0 Hz, 1H), 7.12-7.24 (m, 2H), 7.64 (dq, J=7.8, 1.1 Hz, 2H), 7.75 (d, J=2.0 Hz, 1H), 8.09-8.16 (m, 2H), 8.21 (d, J=2.1 Hz, 1H), 9.70 (s, 1H), 10.23 (s, 1H); MS (ESI−) m/z 433.1 [M−H]$^-$.

Step 4: 3-amino-5-[4-(trifluoromethoxy)benzene-1-sulfonyl]-N'-({[tri(propan-2-yl)silyl]oxy}acetyl)pyridine-2-carbohydrazide 3-Amino-N'-(hydroxyacetyl)-5-[4-(trifluoromethoxy)benzene-1-sulfonyl]pyridine-2-carbohydrazide (0.5315 g, 1.224 mmol, Step 3) was suspended in 10 mL of dichloromethane in a 50-mL round-bottomed flask, and the flask was cooled to 0° C. in an ice bath. Triethylamine (0.341 mL, 2.447 mmol) was added, followed by dropwise addition of triisopropylsilyl trifluoromethanesulfonate (0.660 mL, 2.447 mmol). The reaction mixture was stirred at 0° C. for 15 minutes, at which point the flask was warmed to room temperature and stirred for an additional 2.5 hours. The reaction mixture was quenched by the addition of water. The organic layer was separated, dried over anhydrous sodium sulfate, filtered, and concentrated in vacuo. The residue was purified via flash chromatography, and was eluted with a gradient of 0-2.5% $CH_3OH$ in $CH_2Cl_2$ on a 40 g silica gel column to afford 720 mg of the title compound. $^1$H NMR (400 MHz, DMSO-$d_6$) δ ppm 1.01 (d, J=7.1 Hz, 18H), 1.08-1.19 (m, 3H), 5.03 (s, 2H), 7.26 (s, 2H), 7.60-7.68 (m, 2H), 7.90 (d, J=2.0 Hz, 1H), 8.11-8.20 (m, 2H), 8.41 (d, J=2.0 Hz, 1H); MS (ESI+) m/z 591.1 [M+H]$^+$.

Step 5: 5-[4-(trifluoromethoxy)benzene-1-sulfonyl]-2-[5-({[tri(propan-2-yl)silyl]oxy}methyl)-1,3,4-oxadiazol-2-yl]pyridin-3-amine To a solution of 3-amino-5-[4-(trifluoromethoxy)benzene-1-sulfonyl]-N'-({[tri(propan-2-yl)silyl]oxy}acetyl)pyridine-2-carbohydrazide (0.4638 g, 0.785 mmol, Step 4) and triethylamine (0.219 mL, 1.570 mmol) in dichloromethane (1.8 mL) was added p-toluenesulfonyl chloride (0.299 g, 1.570 mmol), and the reaction mixture was stirred at room temperature for 3 days. The reaction mixture was then washed with a saturated aqueous solution of $NaHCO_3$. The organic layer was separated, dried over anhydrous sodium sulfate, filtered, and concentrated in vacuo. The residue was purified via precipitation from 3 mL of dimethyl sulfoxide and 3 mL of methanol to provide 268 mg of the title compound. $^1$H NMR (400 MHz, DMSO-$d_6$) δ ppm 1.01 (d, J=7.1 Hz, 18H), 1.08-1.19 (m, 3H), 5.03 (s, 2H), 7.26 (s, 2H), 7.60-7.68 (m, 2H), 7.90 (d, J=2.0 Hz, 1H), 8.11-8.20 (m, 2H), 8.41 (d, J=2.0 Hz, 1H); MS (ESI+) m/z 573.1 [M+H]$^+$.

Step 6: (5-{3-amino-5-[4-(trifluoromethoxy)benzene-1-sulfonyl]pyridin-2-yl}-1,3,4-oxadiazol-2-yl)methanol To a solution of 5-[4-(trifluoromethoxy)benzene-1-sulfonyl]-2-[5-({[tri(propan-2-yl)silyl]oxy}methyl)-1,3,4-oxadiazol-2-yl]pyridin-3-amine (0.2664 g, 0.465 mmol, Step 5) in tetrahydrofuran (3 mL) was added a solution of tetrabutylammonium fluoride in (1 M in tetrahydrofuran, 0.465 mL, 0.465 mmol) dropwise, and the reaction was stirred at room temperature for 1.5 hours. The reaction mixture was then partitioned between ethyl acetate and water. The combined organic extracts were dried over sodium sulfate, filtered, and concentrated in vacuo. The residue was then sonicated in dichloromethane to give a solid, which was isolated via filtration and dried to constant weight to give 168 mg of the title compound. $^1$H NMR (400 MHz, DMSO-$d_6$) δ ppm 4.71 (s, 2H), 5.98 (s, 1H), 7.23 (s, 2H), 7.63 (dq, J=8.9, 1.1 Hz, 2H), 7.87 (d, J=2.0 Hz, 1H), 8.07-8.20 (m, 2H), 8.39 (d, J=2.0 Hz, 1H); MS (ESI-) m/z 414.9 [M−H]$^-$.

Alternative Preparation of 3-amino-5-[4-(trifluoromethoxy)benzene-1-sulfonyl]-N'-({[tri(propan-2-yl)silyl]oxy}acetyl)pyridine-2-carbohydrazide

Step 1: methyl {[tri(propan-2-yl)silyl]oxy}acetate

Methyl 2-hydroxyacetate (CAS: 96-35-5, 80 g, 888.9 mmol) was mixed with imidazole (CAS: 288-32-4, 182 g, 2.7 mol) in dry N,N-dimethylformamide (1 L). To this solution, triisopropylsilyl chloride (CAS: 13154-24-0, 228 mL, 1.1 mol) was added. The resulting mixture was stirred at ambient temperature under a nitrogen atmosphere. After overnight stirring, the mixture was quenched with saturated aqueous $NaHCO_3$ (1.5 L) and subsequently extracted with diethyl ether. The combined organic fractions were washed with 2 M HCl (1.4 L, 2.8 mol), water (0.5 L) and brine (1 L). The organic layer was then dried over $Na_2SO_4$, filtered and concentrated to dryness to afford 199 g of title compound that was used as such.

Step 2: 2-{[tri(propan-2-yl)silyl]oxy}acetohydrazide

Methyl {[tri(propan-2-yl)silyl]oxy}acetate (199 g, 808.4 mmol) was dissolved in tetrahydrofuran (1 L). Aqueous hydrazine solution (35% w/w, 200 mL, 2.2 mol) was added, and the mixture was refluxed overnight. Next, the mixture was quenched with $NaHCO_3$ (1.5 L) followed by extraction with ether (4×500 mL). The combined organic fractions were dried over $Na_2SO_4$, filtered and concentrated to dryness to afford 191 g of crude material. The crude material was precipitated overnight from ethyl acetate/heptane (500 mL, 5/95) to afford 122 g of title compound.

Step 3: 3-amino-5-[4-(trifluoromethoxy)benzene-1-sulfonyl]-N'-({[tri(propan-2-yl)silyl]oxy}acetyl)pyridine-2-carbohydrazide 3-Amino-5-(4-trifluoromethoxy-benzenesulfonyl)-pyridine-2-carboxylic acid (107.3 g, 296.4 mmol) was mixed with 2-{[tri(propan-2-yl)silyl]oxy}acetohydrazide (87.5 g, 355.7 mmol), 1-(3-dimethylaminopropyl)-3-ethylcarbodiimide hydrochloride (EDCI, CAS: 1892-57-5, 68.3 g, 355.7 mmol) and 4-dimethylaminopyridine (CAS: 1122-58-3, 43.4 g, 355.7 mmol) in dichloromethane (2 L). The resulting mixture was stirred at ambient temperature overnight. Next, the reaction was quenched with 1 N aqueous HCl solution (1 L, 1 mol) and extracted with dichloromethane. The organic layer was washed with brine and $H_2O$, dried over $Na_2SO_4$, filtered and concentrated to dryness to afford 186.5 g of title compound which was used as such.

Example 2

(5-{3-amino-5-[4-(trifluoromethoxy)benzene-1-sulfonyl]pyridin-2-yl}-1,3,4-oxadiazol-2-yl)methyl (dimethylamino)acetate (5-{3-Amino-5-[4-(trifluoromethoxy)benzene-1-sulfonyl]pyridin-2-yl}-1,3,4-oxadiazol-2-yl)methanol (1.5 g), N,N-dimethylglycine hydrochloride (1.5 eq.), 1-ethyl-3-[3-(dimethylamino)propyl]-carbodiimide hydrochloride (1.7 eq.) and 4-(dimethylamino) pyridine (0.25 eq.) were combined and suspended in dichloromethane (30 mL). The suspension was stirred at room temperature. Analysis after 1 hour showed 2.5% starting material, and 97.5% title compound. Additional 1-ethyl-3-[3-(dimethylamino)propyl]-carbodiimide hydrochloride (0.2 eq.) and dichloromethane (15 mL) were added and the reaction mixture was stirred at room temperature overnight. Saturated aqueous NaHCO$_3$ solution (60 mL) was added and the layers were separated. The organic layer was washed with saturated NH$_4$Cl solution (60 mL), dried over Na$_2$SO$_4$, filtered and concentrated to provide the title compound (93% yield). The material was purified by flash chromatography (dichloromethane/methanol with triethylamine) to provide the title compound. $^1$H NMR (400 MHz, DMSO-d$_6$) δ ppm 8.44 (d, J=2.0 Hz, 1H), 8.20-8.13 (m, 2H), 7.93 (d, J=2.1 Hz, 1H), 7.71-7.64 (m, 2H), 7.29 (s, 2H), 5.47 (s, 2H), 3.29 (s, 2H), 2.25 (s, 6H); MS (ESI+) m/z 502.0 [M+H]$^+$.

Example 3

(5-{3-amino-5-[4-(trifluoromethoxy)benzene-1-sulfonyl]pyridin-2-yl}-1,3,4-oxadiazol-2-yl)methyl 3-(dimethylamino)propanoate (5-{3-Amino-5-[4-(trifluoromethoxy)benzene-1-sulfonyl]pyridin-2-yl}-1,3,4-oxadiazol-2-yl)methanol (1.5 g), N,N-dimethyl-β-alanine hydrochloride (1.1 eq.), 1-ethyl-3-[3-(dimethylamino)propyl]-carbodiimide hydrochloride (1.7 eq.) and 4-(dimethylamino) pyridine (0.25 eq.) were combined and suspended in dichloromethane (30 mL). The mixture was stirred at room temperature. Analysis of the reaction mixture after 1 hour showed 3.5% starting material left, and 95.9% title compound. 1-Ethyl-3-[3-(dimethylamino)propyl]-carbodiimide hydrochloride (0.2 eq.) and dichloromethane (15 mL) were added and the reaction mixture was stirred at room temperature overnight. A saturated aqueous Na$_2$CO$_3$ solution (60 mL) was added and the layers were separated. The organic layer was washed with aqueous saturated NH$_3$Cl solution (60 mL), dried over Na$_2$SO$_4$, filtered and concentrated to provide crude title compound (93% yield). The crude material was purified by flash chromatography (dichloromethane/methanol with triethylamine) to provide the title compound (>98% by LCMS). $^1$H NMR (400 MHz, Chloroform-d) δ ppm 8.51 (d, J=1.9 Hz, 1H), 8.07 8.00 (m, 2H), 7.70 (d, J=2.0 Hz, 1H), 7.42 7.34 (m, 2H), 6.28 (s, 2H), 5.40 (s, 2H), 2.69 2.55 (m, 4H), 2.24 (s, 6H); MS (ESI+) m/z 516.0 [M+H]$^+$.

Example 4

(5-{3-amino-5-[4-(trifluoromethoxy)benzene-1-sulfonyl]pyridin-2-yl}-1,3,4-oxadiazol-2-yl)methyl (2S)-2-amino-3-methylbutanoate Step 1: Preparation of (5-{3-amino-5-[4-(trifluoromethoxy)benzene-1-sulfonyl]pyridin-2-yl}-1,3,4-oxadiazol-2-yl)methyl (2S)-2-[(tert-butoxycarbonyl)amino]-3-methylbutanoate A reactor was charged with (5-{3-amino-5-[4-(trifluoromethoxy)benzene-1-sulfonyl]pyridin-2-yl}-1,3,4-oxadiazol-2-yl)methanol (Example 1, 1.0 equivalent), 4-(dimethylamino) pyridine (0.3 equivalents), N-(tert-butoxycarbonyl)-L-valine (1.5 equivalents), and acetonitrile. The resulting mixture was stirred at ambient temperature. 1-Ethyl-3-[3-(dimethylamino)propyl]-carbodiimide hydrochloride (1.5 equivalents) was charged through a solid addition funnel. The reaction mixture was adjusted to an internal temperature of approximately 25° C., and stirred for 2 hours. An aqueous solution of diluted phosphoric acid (0.15 M) was added into the reaction mixture over approximately 2 hours while maintaining the internal temperature of approximately 25° C. The mixture was stirred at approximately 25° C. for approximately 8 hours, followed by slow addition of a second portion of an aqueous solution of diluted phosphoric acid. The resulting slurry was stirred at 25° C. for approximately 3 hours and was filtered. The solid was washed with purified water and dried at 50° C. under vacuum for approximately 24 hours to provide the title compound (91.9% yield).

Step 2: Preparation of (5-{3-amino-5-[4-(trifluoromethoxy)benzene-1-sulfonyl]pyridin-2-yl}-1,3,4-oxadiazol-2-yl)methyl (2S)-2-amino-3-methylbutanoate A reactor was charged with (5-{3-amino-5-[4-(trifluoromethoxy)benzene-1-sulfonyl]pyridin-2-yl}-1,3,4-oxadiazol-2-yl)methyl (2S)-2-[(tert-butoxycarbonyl)amino]-3-methylbutanoate (1.0 eq.) and dichloromethane. The reaction mixture was stirred and the temperature was adjusted to approximately 15° C. Trifluoroacetic acid was added slowly while maintaining the internal temperature below 25° C. The reaction mixture was stirred at an internal temperature of approximately 20° C. for about 10 hours when 5-{3-amino-5-[4-(trifluoromethoxy)benzene-1-sulfonyl]pyridin-2-yl}-1,3,4-oxadiazol-2-yl)methyl (2S)-2-[(tert-butoxycarbonyl)amino]-3-methylbutanoate was consumed (≤0.5% via reverse phase HPLC). The mixture was transferred and quenched into a pre-cooled mixture of dichloromethane and 10% potassium phosphate aqueous solution while maintaining an internal temperature of approximately 20° C. The mixture was stirred at an internal temperature of approximately 20° C. for about 30 minutes, and was allowed to settle. The organic phase was separated, washed with a solution of saturated aqueous sodium chloride, and dried and filtered through a layer of magnesium sulfate. The layer of magnesium sulfate was rinsed with dichloromethane. The combined organic fractions were concentrated under vacuum. A solvent switch to isopropanol was performed by adding isopropanol as the dichloromethane was distilled. The temperature of the resulting slurry was adjusted to approximately 20° C. and was stirred for 1 hour. The slurry was cooled to approximately 5° C. and mixed for at least 1 hour. The solid was collected by filtration, and washed with isopropanol. The wet-cake was dried under vacuum at 50° C. for approximately 24 hours to afford the title compound (86% yield). $^1$H NMR (400 MHz, DMSO-d$_6$) δ ppm 0.89 (d, J=6.8, 3H), 0.84 (d, J=6.8, 3H), 1.73 (s, 2H), 1.89 (m, 1H), 3.23 (d, J=5.4 Hz, 1H), 5.48 (d, J=14.2 Hz, 1H), 5.51 (d, J=14.2 Hz, 1H), 7.29 (s, 2H), 7.68 (m, 2H), 7.94 (d, J=2.0 Hz, 1H), 8.17 (m, 2H), 8.44 (d, J=2.0 Hz, 1H); MS (ESI+) m/z 516.2 [M+H]$^+$; MS (ESI−) m/z 514.1 [M−H]$^-$.

Example 5

Pharmacokinetic Study 1

Purpose of the Study

Evaluate the PK profile of Example 4, which is a prodrug of (5-{3-amino-5-[4-(trifluoromethoxy)benzene-1-sulfonyl]pyridin-2-yl}-1,3,4-oxadiazol-2-yl)methanol, in healthy human adult subjects.

Methods

Two open label Phase 1, first in human studies in adult healthy subjects were conducted to evaluate the safety, tolerability, and pharmacokinetics of single oral doses of Example 1 administered as an oral suspension and prodrug Example 4 capsule, respectively. Subjects were screened and enrolled based on pre-specified criteria for inclusion and exclusion. The safety in subjects was determined by clinical evaluation and by monitoring of laboratory parameters. Blood samples were longitudinally collected at pre-specified time points following the administration of Example 1 or Example 4—Prodrug to measure the plasma concentrations of study drug and determine the pharmacokinetics of Example 1 and Example 4—Prodrug.

Subject Inclusion Criteria

For this study the inclusion criteria includes the following:
1. Able and willing to comply with the protocol requirements and signing the informed consent form (ICF) as approved by the Independent Ethics Committee (IEC), prior to any screening evaluations.
2. Female between 18-65 years of age (extremes included), on the date of signing the ICF, and of
   a. Non-childbearing potential defined as permanently surgically sterile (bilateral oophorectomy, i.e. surgical removal of ovaries, bilateral salpingectomy, or hysterectomy, i.e. surgical removal of uterus), or postmenopausal with no menses for 12 or more months without an alternative medical cause AND a follicle-stimulating hormone (FSH) level >35 IU/L. Subjects must have negative pregnancy tests. For surgical sterilization, documented confirmation will be required; OR
   b. Childbearing potential, willing to comply with the highly effective contraceptive methods prior to the screening visit, and during the entire clinical study. Subjects must have negative pregnancy tests.
3. A body mass index (BMI) between 18-30 kg/m$^2$, inclusive.
4. Judged to be in good health by the investigator based upon the results of a medical history, physical examination, vital signs, 12-lead triplicate ECG, and fasting clinical laboratory safety tests. Clinical laboratory safety test results must be within the reference ranges or test results that are outside the reference ranges need to be considered not clinically significant in the opinion of the investigator.
5. Subject must be able and willing to comply with restrictions on prior and concomitant medications.
6. Nonsmoker and not using any nicotine-containing products. A nonsmoker is defined as an individual who abstained from smoking or nicotine-containing products for at least 1 year prior to first dosing.
7. Negative screen for drugs (amphetamines, barbiturates, benzodiazepines, cannabis, cocaine, opiates, methadone, tricyclic antidepressants) and alcohol.

Single Ascending Dose

Subjects were enrolled in the Single Ascending Dose study and received 250 or 500 mg Example 1, Example 4—Prodrug or Placebo following the consumption of a moderate fat meal. All doses of Example 4 are expressed in dose equivalent of Example 1. Blood samples for determination of Example 1 and Example 4—Prodrug concentrations were collected at 0-hour (pre-dose), 0.25, 0.5, 1, 1.5, 2, 3, 4, 6, 8, 10, 12, 24, 48, 72, 96, 120, 144, and 168 hours after dosing.

Pharmacokinetic Analysis

Plasma concentrations of Example 1 and Example 4—Prodrug were determined using validated methods. The values for the pharmacokinetic parameters of Example 1 or Example 4—Prodrug were determined using noncompartmental methods with WinNonlin Phoenix 8.1.

Results

In each study, a total of six subjects were enrolled and received the single 250 mg or 500 mg dose of Example 1 (total of 12 subjects) or Example 4—Prodrug (total of 12 subjects). Following the administration of Example 4—Prodrug no quantifiable plasma concentrations of Example 4—Prodrug were observed. The pharmacokinetics of Example 1 following the administration of Example 1 or Example 4—Prodrug is provided in Table 4.

Mean (% CV) Example 1 Pharmacokinetic Parameters Following the Administration of a 250 or 500 mg Single Dose of Example 4—prodrug or Example 1 in Healthy Adult Subjects are summarized in Table 4.

TABLE 4

| Pharmacokinetic Parameter | Units | 250 mg | | 500 mg | |
|---|---|---|---|---|---|
| | | Example 4-Prodrug (n = 6 subjects) | Example 1 (n = 6 subjects) | Example 4-Prodrug (n = 6 subjects) | Example 1 (n = 6 subjects) |
| $C_{max}$ | µg/mL | 1.23 (26) | 0.518 (14.0) | 1.87 (42) | 0.633 (18.3) |
| $T_{max}{}^a$ | Hr | 4 (3-4) | 2.5 (1.5-3.0) | 4 (4-6) | 2.5 (1.5-3.0) |
| $t_{1/2}{}^b$ | µg · h/mL | 31.3 (8.10) | 33.2 (27.8) | 27.3 (11.9) | 31.3 (40.7) |
| $AUC_{0-t}$ | µg/mL/mg | 20.6 (32) | 9.21 (26.6) | 30.9 (55) | 14.1 (42.0) |
| $AUC_{inf}$ | µg · h/mL/mg | 21.6 (42) | 9.31 (26.7) | 31.8 (53) | 14.4 (44.3) |

Note:
All doses of Example 4 are expressed in dose equivalent of Example 1.
$^a$Median (minimum-maximum).
$^b$Harmonic mean (pseudo Standard Deviation).

General Conclusions

The exposure of Example 1 increased by approximately 2.4-fold for $C_{max}$ and 2.3-fold for $AUC_{inf}$ following the oral administration of a single dose of 250 mg Example 4—Prodrug compared to when Example 1 parent is administered. For the 500 mg single dose, a similar increase of 3-fold for $C_{max}$ and 2.2-fold for $AUC_{inf}$ of Example 1 was observed following the oral administration of a single dose of 500 mg Example 4—Prodrug compared to when Example 1 is administered.

Further benefits of Applicants' invention will be apparent to one skilled in the art from reading this patent application.

It is to be understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed:

1. A compound which is (5-{3-amino-5-[4-(trifluoromethoxy)benzene-1-sulfonyl]pyridin-2-yl}-1,3,4-oxadiazol-2-yl)methyl (2S)-2-amino-3-methylbutanoate, or a pharmaceutically acceptable salt thereof.

2. (5-{3-Amino-5-[4-(trifluoromethoxy)benzene-1-sulfonyl]pyridin-2-yl}-1,3,4-oxadiazol-2-yl)methyl (2S)-2-amino-3-methylbutanoate.

3. A pharmaceutical composition comprising the compound of claim 1, or a pharmaceutically acceptable salt thereof, in combination with a pharmaceutically acceptable carrier.

* * * * *